United States Patent [19]
Corn

[11] Patent Number: 6,062,216
[45] Date of Patent: *May 16, 2000

[54] SLEEP APNEA DETECTOR SYSTEM

[75] Inventor: Stephen B. Corn, Sharon, Mass.

[73] Assignee: Children's Medical Center Corporation, Boston, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/773,577

[22] Filed: Dec. 27, 1996

[51] Int. Cl.[7] .................................................. A61M 16/00
[52] U.S. Cl. ...................... 128/204.23; 600/529; 600/534
[58] Field of Search ...................... 128/204.23, 204.21, 128/204.18; 600/529, 532, 534, 535, 538, 653.1, 453, 438, 552, 575

[56] References Cited

U.S. PATENT DOCUMENTS

| | | | |
|---|---|---|---|
| 3,373,441 | 3/1968 | Zadig | 346/107 |
| 3,796,208 | 3/1974 | Bloice | 128/721 |
| 3,875,929 | 4/1975 | Grant | 128/653.1 |
| 3,893,111 | 7/1975 | Cotter | 128/653.1 |
| 4,122,427 | 10/1978 | Karsh | 128/721 |
| 4,197,856 | 4/1980 | Northrop | 128/721 |
| 4,350,166 | 9/1982 | Mobassy | 600/532 |
| 4,387,722 | 6/1983 | Kearns | 128/716 |
| 4,777,962 | 10/1988 | Watson et al. . | |
| 4,867,152 | 9/1989 | Kou | 128/721 |
| 4,919,536 | 4/1990 | Komine | 356/28.5 |
| 4,928,703 | 5/1990 | Wong | 600/532 |
| 4,958,638 | 9/1990 | Sharpe et al. | 128/721 |
| 5,208,641 | 5/1993 | Mocker | 356/28 |
| 5,221,956 | 6/1993 | Patterson et al. | 600/653.1 |
| 5,231,591 | 7/1993 | Flewelling et al. | 600/532 |
| 5,309,921 | 5/1994 | Wiener et al. | 600/532 |
| 5,359,404 | 10/1994 | Dunne | 356/5 |
| 5,504,488 | 4/1996 | Henderson et al. | 342/115 |
| 5,521,696 | 5/1996 | Dunne | 356/5.07 |
| 5,528,246 | 6/1996 | Henderson et al. | 342/115 |
| 5,528,518 | 6/1996 | Bradshaw et al. | 364/561 |

OTHER PUBLICATIONS

Feigen, L. et al., "A Method for Detecting and Measuring Frequency of Surface Vibrations Using a Helium–Neon Laser," *Notes, Department of Biophysics and Biomedical Engineering Northeastern Univ.*, pp. 381–382 (Oct. 1968).

Payne, J.P. "The Quality of Measurement," *Joseph Clover Lecture at Research Department of Anaesthetics, Royal College of Surgeons of England.*, vol. 47, pp. 305–322 (Mar. 1970).

Zivi, S.M. et al., "Chest Motion Visualized By Holographic Interferometry," *Med. Res. Eng.*, pp. 5–7 (Jun. 1970).

Girardin, M. et al., "Experimental Study Of Velocity Fields In A Human Nasal Fossa By Laser Anemometry," *Ann. Otol. Rhinol. Laryngol.*, vol. 92, pp. 231–236 (1983).

Low, P.A. et al., "Evaluation of Skin Vasomotor Reflexes by Using Laser Doppler Velocimetry," *Mayo Clin. Proc.*, vol. 58, pp. 583–592 (Sep. 1983).

"Infantile Apnea and Home Monitoring," *National Institutes of Health Consensus Development Conference Statement.*, vol. 6, No. 6, pp. 1–10 (Oct. 1986).

(List continued on next page.)

Primary Examiner—John G. Weiss
Assistant Examiner—VIrendra Srivastava
Attorney, Agent, or Firm—Lahive & Cockfield, LLP; Anthony A. Laurentano

[57] ABSTRACT

An apnea monitor and system for treatment includes a detector in a fixed console that projects a detection beam at a sleep surface. The detection beam is reflected off a patient on the surface and return light is analyzed to develop a signal which varies with external motion of the patient's upper body. The motion signals are then fed to a pattern recognizer which identifies breath signals and analyzes them to detect cessation or excessive pauses in breathing, and trigger an alarm or intervention to restore breathing regularity. The monitor includes a laser for generating radiation. The radiation is reflected from the patient and is directed onto a detector. The detector produces output signals corresponding to the impinging reflected light, which are processed by a control element to determine the change of movement, e.g., the breathing rate, of the patient.

40 Claims, 3 Drawing Sheets

OTHER PUBLICATIONS

Anderson, W. et al., *"Evaluation of a Respiratory Rate Monitor in Postsurgical Patients,"* J. Clin. Anesth., vol. 4, pp. 289–291 (Jul./Aug. 1992).

Healthdyne Technologies., "Smartmonitor® *A Cardiorespiratory Infant Monitoring System Designed for Home Use*" (1996).

SLEEP APNEA DETECTOR SYSTEM

BACKGROUND OF THE INVENTION

The present device relates to instruments and systems for detecting apnea and respiratory arrest, and to systems wherein such a detector is used in conjunction with an alarm or a prompt to summon help, jar an individual back to a normal breath cycle, or otherwise respond to or treat the detected condition.

Breathing is normally characterized by a more or less regular rhythm of inhaling and exhaling. Apnea, or cessation of respiratory airflow, is a condition in which pauses of greater or lesser duration occur. These pauses may be of such length as to appear to be, or to actually amount to complete cessation of breathing. Apnea may be caused by a number of different mechanisms including obstructive episodes in the upper airway, by neurologic or disease-mediated lack of diaphragmatic motion, or by a combination of these factors. Although poorly understood, sleep apnea has been associated with sudden infant death syndrome (SIDS) which kills hundreds of infants annually. In addition, children are particularly vulnerable to apnea after general anesthesia, and both children and adults receiving epidural narcotics and local anesthetics are at increased risk of apnea and respiratory arrest.

For the latter group of people, a number of monitoring devices have been developed or proposed. These include respiration monitors which detect the carbon dioxide level in air exhaled by the patient, transcutaneous oxygen monitors or pulse oximetry instruments, as well as diverse instruments which sense motion of the abdomen. Among the latter may be counted an elastic strain-sensing belt that may be worn over clothing, and infrared movement detectors which have been used in research environments. In addition, acoustic detectors configured to detect the sound of breathing have been used together with specially programmed microprocessors to determine when cessation of breath or lapses in the breath rate occur, and to trigger appropriate hospital alarms. U.S. Pat. No. 5,551,418 shows a device for coordinating airway pressure with respiration of the patient, and U.S. Pat. No. 5,546,933 shows a system wherein a positive pressure breathing source is controlled based on detecting flow limitation of an inhalation wave form.

A significant drawback of the strain-sensing belt technique is that it typically requires that the belt be affixed to the patient. The corresponding wires that couple the belt with the detection unit markedly increase the risk that the subject will become entangled in the wires, which is undesirable, especially with small children. Moreover, if the subject is experiencing unrestful sleep which is accompanied by tossing and turning, the wires may detach from the unit or the belt, thereby creating false alarms.

A drawback of the remaining techniques is that movement of the subject interferes with the monitoring of the subject. Consequently, the system may generate false alarms, which are bothersome to the subject and to the attending clinicians in a hospital environment.

In addition to the foregoing approaches specifically related to apnea detection, there exist a number of other techniques for the measurement of motion which have not seen application to apnea detection. Among these techniques should be mentioned Lidar, a radar-like ranging technique which determines the velocity of a moving surface by projecting a short burst of light at an object and determining the round-trip transit time of light reflected off the object and which is returned to a photodetector. This technique has been applied with appropriate timing circuits and detection devices, to determine both the distance and velocity (obtained from the change in distance at two times) for moving objects such as automobiles, for which purpose the technology is similar to radar speed detectors, but is useful generally at lesser ranges. Similarly, reflected light figures in laser Doppler measurements, which rely on the reflection of incident light off of moving surfaces, such as particles in a flow stream. In this case, the light beam is a coherent beam which is preferably continuous, and the motion information is detected by mixing a return beam with a reference beam on a photo-detector and analyzing the detected signal by a Fourier transformation to determine the frequency components present in the return beat signals present in the mixed beam. This measurement technique, laser Doppler velocimetry, has been applied for example to determine the flow velocity of blood in retinal capillaries and in the skin, to measure flow velocity by introducing aerosol particles as reflectors in an airstream, and to measure fluid flow in other situations. The Doppler measurement technique is well adapted to detection of particle motion at velocities well below one meter per second. To applicant's knowledge, however, neither up these techniques have been applied to any form of patient breath monitoring.

In general, it is desirable that a sleep apnea monitor be non-invasive, and, if attached to the patient, that it employ sensing units which are not subject to entanglement or constriction, and further pose no hazard of laceration, suffocation, or electrocution. In addition, such a sensor should be of general applicability so that for example the presence of a particular incision or operative trauma does not preclude use of the monitor. There remains a need for such a general apnea monitor.

Accordingly, it would be desirable to provide an apnea detection and treatment system of general applicability which is safe, non-invasive, and effective.

SUMMARY OF THE INVENTION

The present invention provides in accordance with a basic embodiment an apnea monitor and system for treatment, wherein a detector in a fixed console projects a detection beam at a sleep surface on which a subject lies. The detection beam is reflected off a surface of the patient and return light is analyzed to develop a signal indicative of the external motion of the patients upper body. The motion signals are then fed to a filter or pattern recognition module which identifies breath signals and analyzes the breath signals to detect apnea. Upon detection of a cessation or excessive pause in breathing, an alarm or intervention signal is applied to alert the patient so as to restore breathing regularity. In one embodiment, an auditory prompter is mounted in the patient's ear and is activated by the apnea detection signal to emit an acoustic stimulus which is heard by the wearer but is inaudible to others. This embodiment provides a prompt or stimulus to restore breathing regularity without requiring the intervention of a spouse or parent (in a domestic situation) or medical personnel (in a hospital or clinic situation). In another embodiment, the detection signal can control a piece of hospital equipment, such as a positive pressure respirator/ventilation system, in which case the pressure pulses are keyed to the breathing cycle of the patient. In this case, the detection unit can include further filters or a module implementing detection algorithms which identifies relevant portions of the breath cycle to synchronize the pressure ventilator with the patient's inhalation and exhalation. In still a further embodiment, the module emits a first apnea detection signal which initiates a patient prompt or a passive signal, such as a quiet prompter audible only to the patient, or a local warning light, and continued cessation of breathing next causes a second detection signal to trigger an alarm, such as a blinking light or buzzer at a nursing station associated with the patient location, or at the patient location, which would also include a tactile sensor.

In a preferred embodiment, the motion detector operates by employing a laser to illuminate the patient, collect return or reflected light along one or more paths, and perform a Doppler analysis of the reflected light, for example, by applying a digitally implemented fast Fourier transform to a collection of measurement signals which are obtained by mixing light signals, such as the illumination source light and the collected return image light, on a photo-detector. The Fourier transform produces a small set or band of discrete frequency and amplitude values which collectively represent the velocity of moving portions of the chest wall, as well as other small motion artifacts of the patient's upper body. These artifacts include movement of head or limbs, movement or twitching of facial or neck muscles, and larger more abrupt motions of the patient's body. The set of frequency data are passed to a filter or pattern recognition unit which identifies those frequencies or groups of frequencies characteristic of the breathing process, and develops a breath signal roughly correlated with repetitive cycles of the inhalation and exhalation which cause the observed motion. Thus, the detector projects a light field and detects apnea events in the return light.

An apnea detection system operates on the inhalation and exhalation signal to determine when a pause of greater than a preset duration has occurred in the breathing cycle and in that case to activate the alarm or prompt signals. For use with pulse pressure ventilators, the breathing cycle signals are also processed to provide the traditional synchronization points for this external machine.

In various other embodiments, rather than Fourier transform processing, the detector may operate directly on image light, for example by forming an image comprised of a speckle pattern made by the reflected laser light mixed with source light on a video sensor or a charge-coupled device (CCD). In this case, the continuously changing speckle pattern consisting of bright and dark speckles is analyzed by an image analysis protocol which rejects artifacts of local motion represented by localized changes of short duration, such as from twitches and the like, as well as artifacts of abrupt motion representative of major body motions occurring at a rate too fast to be associated with the breath cycle. The remaining slowly evolving patterns of speckle dots are analyzed to develop a general amplitude of breathing cycle motion. In various other embodiments, one or more additional sensors such as acoustic sensors that detect breath sounds can be used to provide additional information and allow differentiation of inhalation and exhalation cycles, as well as greater sensitivity to events such as abrupt airway obstruction. These acoustic signals are then also subject to pattern recognition and linked to the alarm states of the device.

According to the present invention, a non-invasive apnea monitor for monitoring breathing of a subject includes an illumination element, such as a laser, for producing radiation within a selected wavelength range, a projection element optically coupled to the laser for projecting the radiation towards the subject, and a determination element for determining a change in position of an area of the subject. The change in position is indicative of the breathing rate of the subject.

According to one aspect, the determination element includes a detector for detecting the laser-generated radiation reflected from the subject. The detector generates, according to one practice, electrical output signals in response to the reflected radiation incident thereupon. A processor in circuit with the detector processes the electrical output signals to determine the change of position of the subject.

BRIEF DESCRIPTION OF THE DRAWINGS

These and other features of the invention will be understood from the description below taken together with the figures illustrating representative embodiments, wherein.

DESCRIPTION OF ILLUSTRATED EMBODIMENTS

Figures 1, 2A:
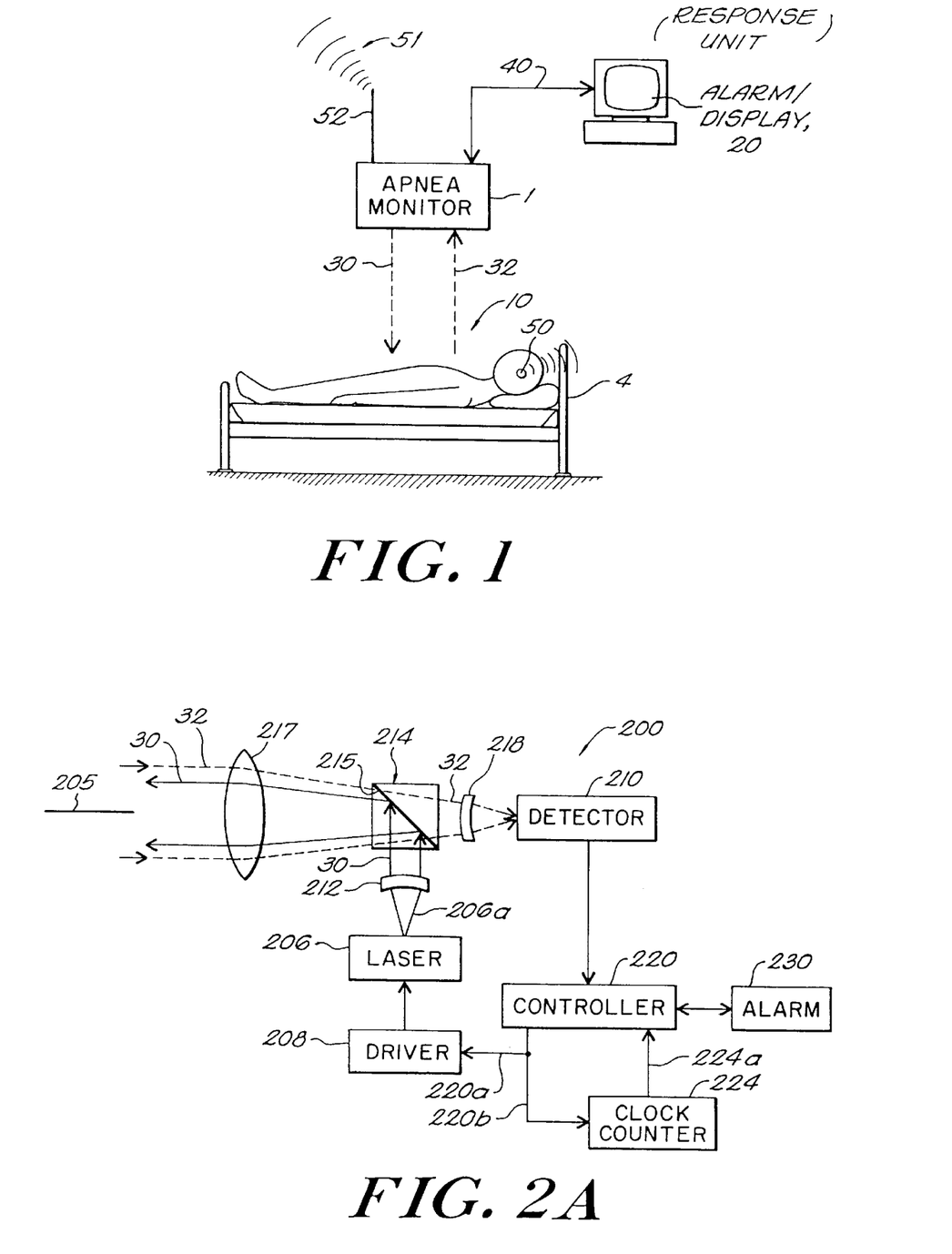
FIG. 1 shows an apnea monitor and treatment system in accordance with the present invention.
FIG. 2A illustrates another embodiment of the monitor of the present invention.

FIG. 1 schematically illustrates a basic embodiment of the apnea monitor 1 of the present invention which, as shown, includes a console or unit which aims a beam 30 of radiating energy at a patient 10 sleeping or immobilized on a bed 11, and receives return reflected energy 32 from the patient. The monitor 1 processes the returned signal and develops an output which as shown is provided along line 40 to a response unit shown as a display 20. The illustrated apnea monitor 1 also broadcasts a response signal 51 from antenna 52, which is received either remotely by responsible medical personnel, or by a prompting transducer unit 50 which can, for example, be mounted or placed in the patient's ear. Such a response unit 50 can include a miniature RF receiver together with audio elements for emitting a detectable sound to prompt the initiation or resumption of breathing cycles.

It will be further understood that the response unit shown as an alarm/display unit 20 is or includes audio alarms, information recording mechanisms such as a strip chart recorder or a digital breath recording database record, blinking warning lights or other appropriate display, alarm or recording equipment. For example, the alarm/display unit 20 can compile a 24-hour breathing record, which lists the time, duration and characteristics of each abnormal breathing event occurring during that period.

Figure 2:
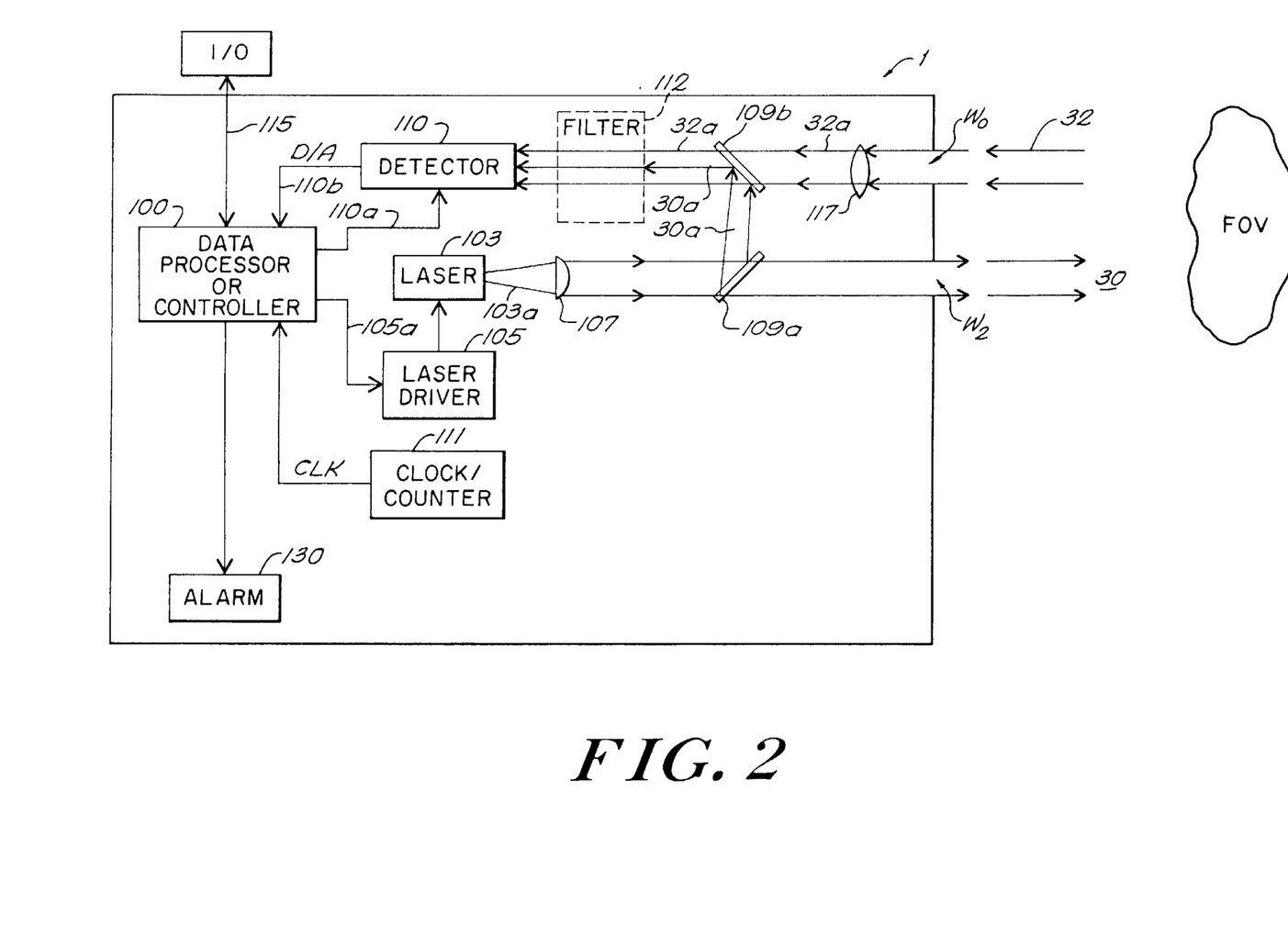
FIG. 2 illustrates operative elements of one embodiment of the monitor of FIG. 1 of the present invention.

FIG. 2 illustrates in greater detail one embodiment of one implementation of the apnea monitor 1. In this embodiment, a data processor or control circuit 100 synchronizes and controls the operation of a laser illumination source 103 and driver 105 which is partially collimated by a projection optics system 107 to produce a slightly divergent output beam 30 which passes through an illumination opening or window $W_L$ of the unit and diverges to a field of view FOV. Instead of the partially collimating projection optics system 107 in the indicated position, the system can include optics located near or in the window $W_L$. Optics 107 can include mirrors, lenses, or suitably recorded hologram lenses, such as thin film phase holograms having the required focusing characteristics for the laser wavelength of source 103. A 1% reflective mirror 109a is also shown, which functions as a beam splitter to provide a portion of the laser illumination light as a reference beam 30a along an optical path to a detector 110. A narrow band filter 112 (shown in phantom) can be positioned in the path of beam 30a to selectively pass light of the laser wavelength to the detector, while blocking unwanted background light.

As further shown in FIG. 2, the light 32 reflected from the field of view FOV enters an observation window $W_O$ where collection optics 117 direct the light as a detection beam 32a through a beam combiner 109b shown as a half-silvered mirror so that detection beam 32a and reference beam 30a both pass through the filter 112 and are combined on the photodetector 110. As also shown in FIG. 2, a clock signal generator 111 provides clock signals to the controller 100, for directly or indirectly (e.g. via a frequency multiplier) generating appropriately timed driver control signals on line 105a for the laser driver, and sampling control signals on line 110a to sample the light intensity at the detector 110 at appropriate intervals. The driver 105 powers the source 103 to generate the radiant energy 103a. The controller 100 interfaces via input/output port 115 with various communications or external devices, such as transmitter and receiver 50 or display 20, FIG. 1, and also with appropriate alarms 130.

Preferably, the signal 110b generated by the detector 110 is processed by sampling the light intensity at a high sampling rate, digitizing the sampled signals and performing a Fourier transform to develop a small set of discrete signals, e.g., a frequency histogram, by which the velocity of the reflection surface, or the velocities of different parts of the reflection surface, are directly represented. In general, for the range of breathing motions considered here, these will be Doppler frequencies in the very low audio or sub-audio range, corresponding to the beat frequencies formed by the chest wall velocities of a fraction of a centimeter per second or more.

According to another practice, the processor 100 counts the zeroes or threshold minions occurring in the output signal 110b of the detector, corresponding to fringes which result from the reference beam 30a and the reflected beam 32a alternately interfering constructively and destructively. This resultant beat frequency is directly proportional to the frequency of the detector output signal 110b, which in turn is proportional to the rate of movement (change in position) of the patient's chest, i.e., breathing rate.

In yet another embodiment, the illumination source can emit a fairly broadband signal or a chirp containing numerous frequencies. The return signal is then processed by a Fourier transferor, much as in the first embodiment, to detect motion of the chest wall.

It will be appreciated that when such Doppler processing is used, the optics and optical paths may take a variety of forms corresponding to known Doppler measurement systems. Thus, for example, the collection window $W_O$ can include two sub windows that subtend different angles with respect to the field of view, and the detector may include several detection surfaces for separately detecting the light along each of the two return paths. This allows the receiver circuit to detect movement along separate directions of motion. Furthermore, the two windows $W_O$, $W_L$ can be replaced by a single window in which a large area, e.g., a 4"×6" holographic lens, collects the return illumination. Such a lens can be formed with a central illumination beam-shaping region and a surrounding light collection region configured to direct return light along the path 32a, thus simultaneously forming the illumination and collection beams.

In the embodiment of FIG. 2, applicant also contemplates that the mixed beam 30a, 32a may be detected on a photodetector 40 which is a video sensor, CCD or other direct spatial light intensity imaging device. In this case, rather than forming a frequency transform representation of breathing movement, the mixed beams form an intricate pattern of interfering light and dark points, called a speckle pattern, which changes as the reflecting surface moves. While the number of speckles is large and even a relatively stationary object like a mattress moves sufficiently to change the speckle pattern, the overall rate of change provides a measure of the type and degree of motion from which a correlated breath rhythm may be derived. For example, the rate of change can be taken to be simply the absolute value sum of new bright speckle spots occurring over a one second time interval, or the rate of change of this function. This measure is readily computed by providing the CCD output, pixel by pixel, to a thresholding circuit followed by comparison to a previous frame and counting of the new bright spots.

In another embodiment of the invention, a motion detector for observing a sleeping patient to detect apnea is provided by a detector which compares each frame of a simple video image with a previous frame and detects small movements. One drawback with this approach is that very slight vertical breathing movements of the chest, as viewed from above, are practically undetectable. Sensitivity to small movements can be improved by using two video images taken from different angles and detecting charges in a pixel-by-pixel difference image. Other image analysis techniques may be used to accentuate the small motions characteristic of breathing, and to develop a signal representative of the breathing cycle.

In order to enhance the reflection of the divergent beam 30 from the patient disposed at the FOV, a suitably reflective surface can be attached or worn by the patient. This reflective surface can be a reflective pad that is affixed to the chest of the patient or a reflective shirt. This is preferably a specular reflector.

FIG. 2A shows another embodiment 200 of the invention which, like the device of FIG. 2, performs Doppler measurements to detect breathing motions. In this embodiment, the laser illumination beam 30 generated by the laser 206 and the return or reflected light 32 travel along a common optical path or axis, e.g., axis 205, through an objective optics system 217. The objective elements 217 can include one or more lens that collimates the light generated by the laser, and which converges the returning light upon a detector 210. For example, the driver circuit 208 drives the laser 206 to generate laser pulses in response to command signals 220a from the controller 220. According to one practice, the laser 206 is a laser transmitting diode which emits repetitive pulses 206a, for example, 380 pulses per second. Suitable laser diodes for use with this embodiment include gallium-arsenide laser diodes having a wavelength of 905 nm, with a peak power output of 50 watts, and a 30–50 ns pulse width.

The laser output pulse 206a is collimated by a suitable lens 212 into a collimated beam 30 which is transferred along an optical path to a beamsplitter 214 having an internal reflective surface 215. The pulse strikes the reflective surface 215 of the beam splitter and is reflected at a right angle along the output axis 205. The beam then passes through the objective optics system 217 and to the field of view. The returning light 32 is then collected by the optics 217 and converged upon the beamsplitter 214. The reflected light preferably passes through the beam splitter 214 and is focused upon a detector 210 by a lens 218. The beam splitter 214 can comprise a pair of right angle prisms that are optically coupled at their diagonal faces to form a cube, or may for example comprise a partially, reflective diagonal mirror or pellicle. Other suitable beam splitters can be employed and are obvious to the ordinarily skilled artisan.

A clock 224 which may further have a timing module with a counter 224a provides a system clock for operating the controller 200. The counter is enabled by the presence of a trigger pulse 220b generated by the controller and conveyed to the input of the module along a command line. The counter output 224a, which may correspond to a timing offset or distance data, is generated by the module and transferred to the controller 200 along a suitable data link. The counter may be stopped by a control signal from the controller, which according to one practice signifies the arrival of the reflected beam at the detector 210. In that case, in operation, the elapsed time between the transmission of the laser energy from the transmitting laser 206 and reception by the detector 210 is successively determined and stored by the controller, to provide ranging and differential chest wall velocity information. Preferably, however, the controller operates by simply collecting a plurality of detector measurement signals, and operating in the frequency domain to extract the required information in this case.

A certain amount of reflectance of the illumination within the system results in a mixed beam on the detector 210, and its output is passed to a dedicated controller 220 which effects the necessary sampling and signal processing to produce the Doppler output, e.g. a frequency histogram indicative of breathing motion slow displacement. Controller 220 may for example include a simple vector processor and memory, for performing a fast fourier transform of each data set, and the controller includes suitable control functions for coordinating the laser driver and running the alarm.

To activate the alarm 230, the controller generates a signal along a data line and is received by the alarm, which is actuated. The alarm can be a visual alarm, such as an LED, an audible alarm such as a buzzer, which comprises part of the monitor or is affixed to the patient, FIG. 1, or can be a tactile alarm.

Figure 3:
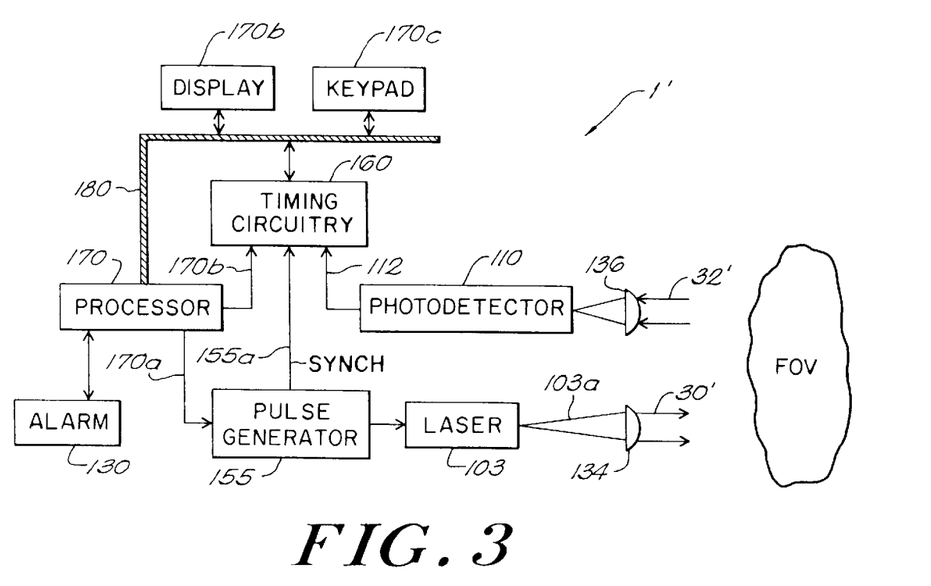
FIG. 3 illustrates still another embodiment of the present invention, which is especially useful for artifact detection.

FIG. 3 illustrates another embodiment 1' of the apnea detection system of the present invention, which operates on a different detection principal. As in the embodiment of FIG. 2, an illumination beam 30' is formed by a laser 103 and a collected beam 32' is directed to a photodetector 110, However, in this embodiment the illumination takes the form of short pulses which are sent at precise starting times determined by a pulse generator/synchronizer 155. In this embodiment the collected return light 32' is focused on a photodetector 110 which produces an output that is fed, after suitable signal shaping, to a timing compactor circuitry or intervalometer 160 which, in addition, receives a replica of the original output trigger signal as a start-of-interval synchronization signal on line 155a. The time interval between transmission and detection is measured by the timing or intervalometer circuit 160. A processor 170 equipped with suitable pattern recognition software processes the detected measurements and produces appropriate alarm 130 or display outputs, e.g., display monitor 170b.

A first optical collimator 134 is optically aligned with the laser pulse 103a generated by the laser source 103 for directing at least a major portion of the pulse to the patient disposed in the field of view FOV. The return or reflected light is focused by a second optical element 136 onto a detector, e.g., a photodetector, to generate a timing reference signal. A filter can be provided in circuit with the detector to ensure that the detector only receives light at wavelengths in the expected wavelength band. According to one practice, the filter is a narrow bandpass interference filter.

The operation of the illustrated apnea monitoring system 1' is controlled by the processor 170. The processor 170 is coupled to the pulse generator 155 and to the timing circuit 160 by control lines 170a and 170b, respectively. The processor 170 actuates the laser by instructing the generator 155 to produce a command signal at its output. The actuation of the pulse generator 155 initializes the timing circuit 160 by generating a synch signal 155a. The reflected light 32' incident upon the detector 110 is transformed into a digital signal output signal 112 which is transferred to the timing circuit.

The illustrated timing circuit 160 operates to determine the arrival times of the synch signals 155a and the output signal 112. These times can be stored in either volatile or nonvolatile memory, The processor 170 reads and stores the clock count times from the counters of the timing circuit 170, and computes the time of flight of the laser pulse. From this information, the processor determines the velocity and /or distance traveled by the patient's surface according to any suitable algorithm stored in appropriate memory.

With further reference to FIG. 3, a keypad 170a allows a user to select or adjust detection parameters, so that, for example, the alarm 130 is activated when breathing stops for a selected time, e.g. 10, 15 or 20 seconds. Preferably, the processor 170 implements several signal or interval analysis protocols on the basic measurements made by the intervalometer circuit 160. One such measurement is to process successive output intervals $\Delta t_i$ each representing the round-trip distance to the observed patient, to produce successive difference measurements, which thus each represent the velocity of movement of the patient or patient's surface. However, since the monitor will in general be no more than several meters from the patient, the first (distance) interval is only around ten nanoseconds and the second (velocity) difference time interval is quite small. Accordingly, a second form of measurement protocol contemplated for this embodiment is to have the processor 170 perform more complex analysis of sets of signals to detect a signal pattern indicative of breathing, for example, by curve fitting, smoothing, measuring the variance, or other signal measurements correlated with the breathing cycle. For example, the processor 170 can detect the stationary intervals at the end of each breath cycle, and trigger the 130 alarm when their periodicity fails.

Figure 4:
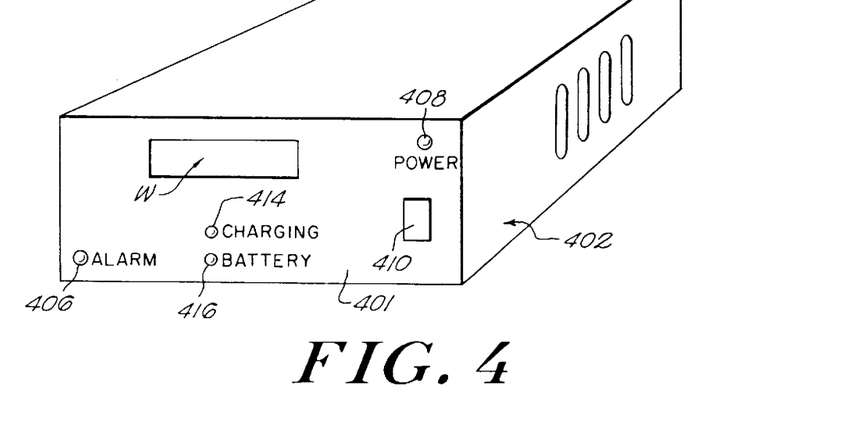
FIG. 4 illustrates one embodiment of the monitor housing showing its external appearance.

FIG. 4 shows the general shape of an apnea detection console 400 useful in accordance with any of the above embodiments. As shown, the console 400 includes a housing 402 that forms an enclosed unit with a window W which functions as the illumination and detection aperture(s). The assembly can be mounted at a fixed position relative to the patient where it is connected to a power source, with the window W directed at the patient. As will be understood from the specific drawings discussed above, the console may incorporate, or attach to, warning lights or displays, or may connect via wire or radiant coupling, to such warning or other prompting devices. For example, the console 400 can include an audible alarm, a visual alarm 406, and the like. The console can further include a visual power indicator 408 to indicate when the console is turned on. A turn on switch 410 actuates the unit. Other visual indicators can e incorporated into the front face 401 of the console 400, such as a charging indicator 414 to indicate when the unit is charging, and a battery indicator 416 to indicate when the unit is consuming battery power.

The illustrated console 400 preferably complies with all applicable federal and state regulations concerning laser powered instruments, such as 21 CFR Part 1040, and more particularly apnea monitors, such as 21 CFR Part 896. For example, the apnea console (monitor) 400 is configured to detect central or diaphragmatic breathing cessation, obstructive breathing cessation or a mixture of the two. The monitor preferably activates an alarm when the cessation period does not exceed 20 seconds, and the alarm is triggered within 1 second after the preset time limit has expired. The audible indicators preferably conform to the decibel, duration and frequency standards required by law.

The console 400 can include appropriate circuitry to undergo a self-diagnostic test, and is preferably configured to include a backup power source, such as a battery.

In each of the foregoing embodiments, the detector (monitor) 400 operates non-invasively to illuminate a field of view at a fixed distance, typically from a ceiling-, wall- or stand-mounted console directed at the top surface of a bed, and analyzes the return signal to detect breathing motion. No wires, cables or sensors directly contact the patient, and the breathing detection is carried out with non-invasive, low power energy. When a laser beam is used, its wavelength may be selected to be invisible (e.g. infrared) or to be highly distinct from the spectral range of other light sources in the room.

The invention may also be carried out using ultrasound instead of laser motion detection. In this case no optical lenses are used; instead an ultrasound radiating antenna-like (e.g., shaped) transducer radiates a preferably continuous beam of ultrasound, for example in the 25 kHz–500 kHz range or higher, and a receiving transducer or transducer array develops one or more electrical output signals indicative of the reflected energy, which shifts slightly from the incident frequency due to breathing motion. As in the embodiment of FIG. 2 a frequency histogram is developed, with the frequencies corresponding to the slow displacements characteristic of normal breath, and the absence of the characteristic frequency from the detected signal for a time interval longer than 5, 10, 15 or 20 seconds triggers the warning or prompt alarms.

In each of the above embodiments, the detector relies on the detection of low level signals to monitor signal responses correlated with breathing. Because the breathing motions are small, several of these signals may provide information that is relatively masked or difficult to interpret. However, because it is only necessary to detect long delays or lapses in breathing, the detector may accumulate signals for several seconds, and may perform various forms of numerical analysis to derive its breath detection reading. In a further embodiment of the invention this capability is further enhanced by providing "expert system" signal analysis, in which a user input may further confirm that a detected pattern is to be considered a representative breath pattern, and the recognition module is trained to recognize breath intervals and apnea episodes. The detector then compares a detected pattern to the stored confirmed pattern to more quickly identify breath segments, to recognize dangerous premonitory patterns such as a progressive lengthening of inter-breath intervals, and to effect particular alarms appropriate to the situation.

Moreover, the above described systems can be easily incorporated into an apnea monitor to provide a laser or ultrasound apnea device that monitors a patient's breathing by detecting changes in movement, and thus the velocity of a portion of the patient, such as the chest. The detected rate of movement can be correlated with previously stored breathing data specific to the patient, or with other pre-stored data, or can store breathing data "on-the-fly" The monitor triggers an alarm to initiate prompt intervention of the breathing cessation or abnormality during the event.

The invention being thus disclosed and various embodiments described, further variations and modifications will occur to those skilled in the art, and all such variations and modifications are considered to lie within the scope of the invention, as defined by the claims appended hereto.

Having described the invention, what is desired to be secured by Letters Patent is:

I claim:

1. An apnea monitor for monitoring breathing of a subject, said monitor comprising illumination means for producing radiation within a selected wavelength range, projection means for projecting the radiation towards the subject, motion determination means for non-invasively determining a change in position of an area of the subject on the basis of changes in radiation reflected by a surface that moves as a result of the subject's breathing, and breathing rate determination means for determining the breathing rate of the subject in response to the change in position of the subject.

2. The apnea monitor of claim 1, wherein the motion determination means comprises a detector for detecting laser-generated radiation reflected from the subject, the detector producing electrical output signals in response to the reflected radiation incident thereupon, and a processor in circuit with the detector for processing the electrical output signals to determine the change of position of the subject.

3. The apnea monitor of claim 1, wherein the illumination means emits laser radiation along a first axis, said monitor further comprising an optical network optically coupled to the laser and having a first optical element for directing a portion of the laser radiation to the motion determination means to form a reference beam.

4. The apnea monitor of claim 3, wherein the motion determination means comprises a detector positioned to receive the reference beam and for detecting the laser-generated radiation reflected from the subject, the detector including means for combining the reflected radiation and the reference beam, and means for generating an electrical signal representative of a beat frequency corresponding to the Doppler shift between the reference beam and the radiation reflected from the subject, and a processor in circuit with the detector for correlating said beat frequency to apnea of the subject.

5. The apnea monitor of claim 4, wherein the processor includes means for counting extrema in the electrical signal generated by the detector, corresponding to interference fringes resulting from the reference beam and the reflected radiation, and means for generating a signal indicative of changes in position of the subject, the processor determining apnea from lapses in said changes in position.

6. The apnea monitor of claim 4, wherein the output signal generated by the detector has a frequency dependent upon the beat frequency between the reflected radiation and the reference beam, which in turn is dependent upon the breathing rate of the subject.

7. The apnea monitor of claim 3, wherein the first optical element is a beamsplitter.

8. The apnea monitor of claim 2, further comprising a filter optically coupled to the detector for filtering ambient light.

9. The apnea monitor of claim 1, further comprising means for driving the laser to produce the radiation.

10. The apnea monitor of claim 1, further comprising an alarm for alerting one of the subject and another person of an alarm condition.

11. The apnea monitor of claim 10, wherein the alarm is an alarm selected from among tactile audible and visual alarms.

12. The apnea monitor of claim 1, further comprising means for transmitting an alarm signal to a location remote from the monitor to alert another person of an alarm condition.

13. The apnea monitor of claim 2, further comprising counter means in circuit with the processor for counting the time between the laser-generated radiation and the reflected radiation detected by the detector.

14. The apnea monitor of claim 2, wherein the detector is a photodetector.

15. The apnea monitor of claim 1, wherein the motion determination means includes means for correlating laser-generated radiation reflected by the subject and radiation directly received by the motion determination means from the laser to determine a beat frequency therebetween.

16. The apnea monitor of claim 1, further comprising a first optical element optically coupled to the laser for collimating the radiation generated by the laser to produce a coherent collimated radiation beam.

17. The apnea monitor of claim 2, further comprising an optical element optically coupled to the detector to converge the reflected radiation thereon.

18. The apnea monitor of claim 1, wherein said motion determination means comprises a data processing system for determining one of the instantaneous distance between the monitor and the selected area of the subject, the rate of movement of the subject, and the breathing rate of the subject.

19. The apnea monitor of claim 1, wherein the motion determination means comprises a data processing system having input-output means for allowing the input of user-selected data and for allowing the transfer of data from the processing system.

20. The apnea monitor of claim 19, wherein the data processing system further comprises a processor, and memory in circuit with the processor for storing data and a program for execution by the processor, the program upon execution determining one of the breathing rate, the change in position, a breathing pattern of the subject, and an apneic period.

21. The apnea monitor of claim 20, further comprising an alarm in circuit with the processing system for alerting one of the subject and another person of an alarm condition, the processing system generating an alarm output signal, wherein the alarm produces one of an audible signal, a visual signal and a tactile signal in response to the alarm output signal.

22. The apnea monitor of claim 1, wherein said illumination means, illuminates with ultrasonic wave energy and wherein said determination means determines a change by Fourier processing of a set of measurements of ultrasonic energy reflected from the subject.

23. The apnea monitor of claim 1, wherein said illumination means includes a laser.

24. A non-invasive method for monitoring breathing of a subject, comprising the steps of illuminating the subject with radiated energy from an external radiation source, detecting radiated energy reflected from a surface that moves as a result of breathing by the subject, and processing the detected energy to identify motions indicative of the breathing rate of the subject.

25. The method of claim 24, wherein the external radiation source includes a laser and the energy is laser light and the steps of detecting and processing comprise detecting laser-generated radiation reflected from the subject and producing electrical output signals in response to the reflected radiation incident thereupon, and processing the electrical output signals to determine change of position of the subject.

26. The method of claim 24, further comprising the step of driving a laser to produce the radiated energy.

27. The method of claim 24, further comprising the step of alerting one of the subject and another person of an alarm condition in response to a cessation of breathing or change in the breathing rate.

28. The apnea monitor of claim 1, wherein said breathing rate determination means comprises a detector positioned to receive the reflected radiation from the subject, said detector generating an output signal in response to said movement, and a processor in circuit with the detector for correlating said output signal to said breathing rate of the subject.

29. The apnea monitor of claim 1, wherein said breathing rate determination means comprises a processor in circuit with the motion determination means for correlating said change in position to said breathing rate of the subject.

30. The apnea monitor of claim 1, wherein said breathing rate determination means comprises a data processing system for storing data associated with the change in position of the subject determined by said motion determination means, and a program for execution by the processor, the program upon execution determining the breathing rate or pattern of the subject to detect an apneic period.

31. The method of claim 24, wherein the steps of illumination comprises the step of emitting laser radiation along a first axis with a laser, optically coupling an optical network with the laser, said optical network including a first optical element for directing a portion of the laser radiation to form a reference beam.

32. The method of claim 31, wherein the step of detecting comprises the steps of positioning a detector to receive the reference beam and for detecting the laser-generated radiation reflected from the subject.

33. The method of claim 32, further comprising the steps of combining the reflected radiation and the reference beam, and determining a beat frequency corresponding to a Doppler shift that occurs between the reference beam and the radiation reflected from the subject, wherein said beat frequency corresponds to said change in position of the subject.

34. The method of claim 33, wherein said step of processing further comprises the step of providing a processor in circuit with the detector for correlating said beat frequency to apnea of the subject.

35. The apnea monitor of claim 34, wherein the step of processing further comprises the steps of counting extrema in an electrical signal generated by the detector, said extrema corresponding to interference fringes resulting from the reference beam and the reflected radiation, and generating a signal indicative of changes in position of the subject, the processor determining apnea from lapses in said changes in position.

36. A method for monitoring breathing of a subject to detect an apnea event, comprising the steps of illuminating the subject with radiation from a laser, collecting return radiation reflected from a surface of the subject, directing the collected laser radiation onto a detector, generating an output signal with the detector indicative of movement or lack of movement of the subject as a function of breathing of the subject, and processing the output signal to determine the breathing rate of the subject.

37. The method of claim 36, further comprising the step of performing a Doppler shift analysis of the laser radiation reflected from the subject.

38. The method of claim 37, further comprising the step of determining breathing rate of the subject from the Doppler analysis of the reflected radiation.

39. The method of claim 36, further comprising the steps of analyzing a speckle pattern generated by the reflected radiation, and determining the breathing rate of the subject from said speckle pattern.

40. The method of claim 36, further comprising the step of providing a control circuit for controlling the operation of the laser.

* * * * *

UNITED STATES PATENT AND TRADEMARK OFFICE
CERTIFICATE OF CORRECTION

PATENT NO.   : 6,062,216
DATED        : May 16, 2000
INVENTOR(S)  : Corn

It is certified that error appears in the above-identified patent and that said Letters Patent is hereby corrected as shown below:

Column 2,
Line 45, replace "patients" with -- patient's --;

Column 10,
Line 12-13, remove "¶ I claim:".

Signed and Sealed this

Twenty-fourth Day of September, 2002

Attest:

JAMES E. ROGAN
Attesting Officer          Director of the United States Patent and Trademark Office